United States Patent [19]

Lazar et al.

[11] Patent Number: 4,581,378

[45] Date of Patent: Apr. 8, 1986

[54] RODENTICIDE COMPOSITIONS COMPRISING AN ARTIFICIAL SWEETENER AND A RODENTICIDE

[75] Inventors: Remus Lazar, Berwyn; Emil P. Lira, Des Plaines, both of Ill.

[73] Assignee: United Agri Products, Inc., Greeley, Colo.

[21] Appl. No.: 347,654

[22] Filed: Feb. 10, 1982

[51] Int. Cl.[4] .................... A01N 25/00; A01N 35/00
[52] U.S. Cl. ................................. 514/681; 514/970; 424/84; 424/17
[58] Field of Search .................... 424/17, 84, 331

[56] References Cited

U.S. PATENT DOCUMENTS

| 3,843,783 | 10/1974 | Burlow | 424/84 |
| 3,929,808 | 12/1975 | Kilbourn et al. | 424/84 |
| 3,929,983 | 12/1975 | Boschetti | 424/17 |
| 3,994,905 | 11/1976 | Kilbourn et al. | 424/84 |
| 4,012,520 | 3/1977 | Youngdale | 424/84 |
| 4,140,778 | 2/1979 | Drelkorn | 424/84 |
| 4,156,714 | 5/1979 | Lechevin et al. | 424/17 |

OTHER PUBLICATIONS

Holcenberg et al.; C.A., vol. 71 100158s (1969).

*Primary Examiner*—Allen J. Robinson
*Attorney, Agent, or Firm*—Willian Brinks Olds Hofer Gilson & Lione Ltd.

[57] ABSTRACT

This application discloses rodenticide compositions containing artificial sweeteners. The disclosed compositions have improved acceptability to the rodents and longer storage life.

3 Claims, No Drawings

RODENTICIDE COMPOSITIONS COMPRISING AN ARTIFICIAL SWEETENER AND A RODENTICIDE

This invention relates to new rodenticide compositions. In particular, this invention relates to sugar-free rodenticide compositions containing artificial sweetners.

The control of rodents, particularly rats and mice, is a widespread problem occurring in residential areas and in rural areas. It is a health problem as well as an interference with the growth of the useful crops.

Rodenticides have been used for a long period of time to control these undesirable pests. The control of rats and mice can be controlled to a high degree with the use of efficient rodenticides. The success of the use of the rodenticide is to a large extent a function of the effectiveness of the active ingredient and of the animal acceptability of the product. The rodent acceptability of the product is related to the taste the rodent has for the product. Naturally, the taste of the rodenticide depends on the selection of the components of the product and the conditions for its preparation.

In addition, the product should have excellent storage stability, i.e. should maintain the level of active ingredient initially in the product and the level of animal acceptability of the product. Rodenticides can be used in various forms such as flaked material, pellets, biscuits, etc. Up until this time, rodenticides have included sugar as an attractant. Sugar has been found necessary in order to make the product more acceptable to the rodent so that it will consume a sufficient quantity of the rodenticide.

Yet the rodenticide compositions containing sugar have been found to have deficiencies, particularly short storage life and a diminishing rodent acceptability.

It is, therefore, an object of this invention to improve the acceptability of rodenticide products to rodents.

Another object of this invention is to prepare rodenticide products that maintain their level of animal acceptability throughout the life of the product.

Still, another object of this invention is to prepare rodenticidal products that maintain their initial content of active ingredient throughout the life of the product.

Other objects of this invention will become apparent from the ensuing description.

Unexpectedly, it has been determined that replacing the sugar, commonly used in the preparation of rodenticides, with an artificial swwetener improves the acceptability of the rodenticides to the rats and mice and stabilizes the initial amount of active ingredients and the initial acceptability of the product to the rodents. Among the artificial sweeteners that can be used in the preparation of the new rodenticide are saccharin and its derivatives such as 5-methyl saccharin,6-chlorosaccharin, sodium and/or calcium saccharin; aspartic acid derivatives such as aspartylrosine methyl ester and aspartylphenylalanine methyl ester; dihydrochalcones such as naringin and neohesperidine dihydrochalcone; glysodic compounds such as stevioside, osladin and glycyrrhizin and cyclamate.

The amount of artificial sweetener that is used in the product will vary with the type of rodenticide being formulated; the active ingredient; the conditions of use e.g. residential, alley, farmland, etc; the effective time period required; the type of rodent being controlled; the other components of the formulation, etc.

Generally, the amount of artificial sweetener to be used in the formulation will vary proportionately with the degree of sweetness of this component. Thus, i.e. only about 10% of the weight of the sugar previously used need be present in the rodenticide when saccharin is to be used in the product. This is advantageous not only because the previous mentioned properties of the product, but also for the need of smaller quantities of materials thus making the final product more compact and more aminable for smaller sizes of pellets which can be easier to distribute in the rodent-infested area.

In preparing the rodenticides of the present invention, normal methods for preparing rodenticides can be used with the only necessary modification being the use of the artificial sweetener rather than the sugar. U.S. Pat. No. 3,843,783 issued Oct. 22, 1974 discloses a method for the preparation of rodenticide pellets. The preparation of baits and tracking powders useful in the control of rodents is described in the literature, e.g. U.S. Pat. No. 3,929,808 issued Dec. 30, 1975; U.S. Pat. No. 4,140,778 issued Feb. 20, 1979 and U.S. Pat. No. 3,994,905 issued Nov. 30, 1976.

Rodenticidal compositions consist of edible materials such as corn meal, barley, wheat, soybeans and oats; preservatives, oil, toxicants and taste enhancers, etc. The amount of these components in the rodenticide composition can vary in accordance with the actual use of the compostion and the presence of the optional ingredients but in general is as follows in weight percentages:

| | |
|---|---|
| inert carrier | 70-95% |
| artificial sweetener | 0.1-3% |
| oil | 1-10% |
| Toxicant | 0.005-0.01% |

It is preferred that the amount of artificial sweetner be between about 0.1 and about 2 weight percent of the rodenticide composition.

Toxicants in use include warfarin, diphacinone, sodium diphacinone, fumarin, fumasol, warfarin in combination with sulfaquinoline, zinc phosphate, strychnine, arsenic, chlorophacinone, coumachlor, coumatetralyl, discoumarin, pival, pivalyn, valone, sodium valone, etc. The preparation of the rodenticide compositions is in the literature. Dry baits can be readily prepared by the use of standard mixers. Pellets are generally formed in extruders in various sizes.

The present invention is not limited to any specific components of the rodenticide composition. It has been found that the use of the artificial sweeteners in the rodenticide formulations is applicable in general to all types of rodenticidal compositions. In order to substantiate the improvements of the present compositions, tests have been performed with three (3) compositions prepared by the following procedure and containing the indicated ingredients:

EXAMPLE 1

| INGREDIENT | WEIGHT % |
|---|---|
| diphacinone | 0.005 |
| grain mix | 87.915 |
| whole ground corn 28.2% | |
| whole ground wheat 22.5% | |
| whole ground soybeans 22.5% | |
| whole ground oats 14.7% | |
| sodium saccharin | 0.500 |

-continued

| INGREDIENT | WEIGHT % |
|---|---|
| soybean oil | 4.400 |
| calcium propionate | 1.000 |
| citric acid | 1.000 |
| sodium chloride | 0.500 |
| butylated hydroxy toluene | 0.025 |
| monosodium glutamate | 0.010 |
| coloring | 0.035 |
| flavoring | 0.010 |
| water | 4.600 |

In preparing the bait, a premix consisting of the diphacinones, monosodium glutamate, butylated hydroxy toluene, coloring, flavoring, salt, citric acid, calcium propionate and sodium saccharin are placed in a mixer for a one hour mixing period. Then the grain mix and soybean oil are mixed with the premix for one hour. Then the entire mixture was extruded, after the addition of water, at a rate of 1500 pounds per hour at a temperature of about 260°–270° F. The residence time in the extruder is about 2–4 minutes. From the extruder, the material is passed into a former at a rate of 1,500 pounds per hour and a residence time of 1.5 minutes and a temperature of 220° F. Pellets of a size 3/16"×1/16" or ½"×½" were obtained from the former, dried and cooled. Tests were performed on three compositions to determine their acceptance to rodents, the mortality of the rodents and the storage stability with the following results:

| COMPO-SITION | TIME (Years) | RESULTS SPECIES | ACCEPTANCE | MORTALITY |
|---|---|---|---|---|
| 1 | Initial | Mice | 42.0% | 100% |
|  | 1 | Mice | 40.8 | 100 |
|  | 2 | Mice | 38.2 | 100 |
| 3 | Initial | Rats | 49.0 | 100 |
|  | 1 | Rats | 50.8 | 100 |
|  | 2 | Rats | 28.7 | 100 |
| 2 | Initial | Mice | 56.8* | 95.0* |
|  | Initial | Rats | 42.4* | 100* |
| 3 | Initial | Mice | 46.3* | 92.5* |
|  | Initial | Rats | 41.6* | 100* |

Mice tests performed using laboratory test method TSD 1.204.
Rat tests performed using laboratory test method TSD 1.203.
*Average of two replicates.

| | COMPOSITIONS | | |
|---|---|---|---|
| | 1 | 2 | 3 |
| Coloring | None | Red Dye | Green Dye |
| Flavoring | Apple | None | Fish Meal |
| Artificial Sweetener | Sodium Saccharin | Sodium Saccharin | Sodium Saccharin |

Optional components in rodenticidal compositions include preservatives such as sodium and calcium propionate, sorbic acid, sodium benzoate, methyl- and ethyl p-hydroxy benzoate and sulfaguinoxiline; anti oxidants such as butylated hydroxy toluene; flavoring such as apple, fish meat, cheese, peanut, etc.; dyes and taste enhancers such as salt, monosodium glutamate, molasses, peanut butter, etc.; acidifiers such as citric acid and sodium citrate; and humectants such as glycols. The presence or absence of these optional components of the rodenticidal compositions does not effect the performance of the present invention. The following examples illustrate some of the rodenticide compositions of this invention:

EXAMPLE 4

| INGREDIENT | WEIGHT |
|---|---|
| Diphacinone | 0.005 |
| Grain mix | 88.5 |
| whole ground corn 80% | |
| whole ground wheat 10% | |
| whole ground soybean 10% | |
| 5-methyl saccharin | 0.5 |
| Soybean oil | 5.0 |
| Dry molasses | 5.0 |
| Sodium propionate | 0.5 |
| Roasted peanut flavor | 0.5 |

EXAMPLE 5

| INGREDIENT | WEIGHT |
|---|---|
| Warfarin | 0.005 |
| Grain mix | 90.0 |
| whole ground corn 60% | |
| whole ground wheat 10% | |
| whole ground soybeans 20% | |
| whole ground oats 10% | |
| Aspartylrosine methyl ester | 0.75 |
| Corn oil | 4.0 |
| Calcium propionate | 1.0 |
| Peanut butter | 0.2 |
| Water | 4.0 |

EXAMPLE 6

| INGREDIENT | WEIGHT |
|---|---|
| Fumarin | 0.005 |
| Whole ground corn | 83.9 |
| Neohesperidine dihydrochalcone | 0.1 |
| Corn oil | 4.0 |
| Sodium propionate | 1.0 |
| Apple flavor | 1.0 |
| Monosodium glutamate | 1.0 |
| Peanut flavor | 5.0 |
| Water | 5.0 |

EXAMPLE 7

| INGREDIENT | WEIGHT |
|---|---|
| Stevioside | 0.005 |
| Grain mix | 85.5 |
| whole ground corn 85% | |
| whole ground wheat 5% | |
| whole ground oats 10% | |
| Peanut oil | 5.5 |
| Peanut flavor | 0.5 |
| Green dye | 0.030 |
| Calcium propionate | 0.50 |
| Glycyrrhizin | 2.0 |
| Citric acid | 1.0 |

EXAMPLE 8

| INGREDIENT | WEIGHT |
|---|---|
| Pivalin | 0.005 |
| Grain mix | 85.5 |
| whole ground oats 10% | |
| whole ground soybeans 10% | |
| whole ground corn 70% | |

| INGREDIENT | WEIGHT |
| --- | --- |
| whole ground wheat 10% | |
| Corn oil | 6.0 |
| Dry molasses | 3.0 |
| Roasted peanut flour | 3.0 |
| Peanut flavor | 0.5 |
| Salt | 0.50 |
| Calcium propionate | 0.50 |
| Sodium citrate | 1.00 |

We claim:

1. A sugar-free rodenticidal composition which comprises a rodenticidal amount of diphacinone, a rodent attracting amount of sodium saccharin, from about 70 to 95 weight percent of grain and from about 1 to about 10 percent of a vegetable oil.

2. The sugar-free rodenticidal composition of claim 1 wherein the sodium saccharin is present in an amount of from about 0.1 to about 2.0 weight percent of the compositions.

3. The sugar-free rodenticidal composition of claim 1 wherein the oil is corn oil.

UNITED STATES PATENT AND TRADEMARK OFFICE
CERTIFICATE OF CORRECTION

PATENT NO. : 4,581,378
DATED : April 8, 1986
INVENTOR(S) : Remus Lazar et al.

Page 1 of 4

It is certified that error appears in the above-identified patent and that said Letters Patent is hereby corrected as shown below:

IN THE SPECIFICATION

In column 1, lines 8-9, please delete "sweetners" and substitute therefor --sweeteners--;

In column 1, line 13, please delete "of the useful" and substitute therefor --of useful--;

In column 1, line 50, please delete "swwetener" and substitute therefor --sweetener--;

In column 1, line 58, please delete "aspartylrosine" and substitute therefor --aspartyltyrosine--;

In column 2, line 10, please delete "aminable" and substitute therefor --amenable--;

In column 2, line 25, please delete "oil" and substitute therefor --oils--;

In column 2, line 28, please delete "compostion" and substitute therefor --composition--;

In column 2, line 38, please delete "sweetner" and substitute therefor --sweetener--;

UNITED STATES PATENT AND TRADEMARK OFFICE
CERTIFICATE OF CORRECTION

PATENT NO. : 4,581,378
DATED : April 8, 1986
INVENTOR(S) : Remus Lazar et al.

It is certified that error appears in the above-identified patent and that said Letters Patent is hereby corrected as shown below:

In column 2, lines 64-68 (in EXAMPLE 1) please indent the ingredients for "grain mix" as follows:

grain mix
    whole ground corn 28.2%
    whole ground wheat 22.5%
    whole ground soybeans 22.5%
    whole ground oats 14.7%

In column 3, line 25, please delete "1/16"" and substitute therefor --3/16"--;

In column 3, lines 52-54 (under COMPOSITIONS), please indent and put in column form as follows:

| Coloring | None | Red Dye | Green Dye |
| Flavoring | Apple | None | Fish Meal |
| Artificial Sweetener | Sodium Saccharin | Sodium Saccharin | Sodium Saccharin |

In column 3, line 62, please insert a comma (,) after the word "fish";

UNITED STATES PATENT AND TRADEMARK OFFICE
CERTIFICATE OF CORRECTION

PATENT NO. : 4,581,378
DATED : April 8, 1986
INVENTOR(S) : Remus Lazar et al.

Page 3 of 4

It is certified that error appears in the above-identified patent and that said Letters Patent is hereby corrected as shown below:

In column 4, lines 9-11 (in EXAMPLE 4), please indent the ingredients for Grain mix as follows:

Grain mix
        whole ground corn 80%
        whole ground wheat 10%
        whole ground soybean 10%

In column 4, lines 23-26 (in EXAMPLE 5), please indent the ingredients for Grain mix as follows:

Grain mix
        whole ground corn 60%
        whole ground wheat 10%
        whole ground soybeans 20%
        whole ground oats 10%

In column 4, lines 52-53 (in EXAMPLE 7), please indent the ingredients for Grain mix as follows:

Grain mix
        whole ground corn 85%
        whole ground wheat 5%
        whole ground oats 10%

UNITED STATES PATENT AND TRADEMARK OFFICE
CERTIFICATE OF CORRECTION

PATENT NO. : 4,581,378
DATED : April 8, 1986
INVENTOR(S) : Remus Lazar et al.

It is certified that error appears in the above-identified patent and that said Letters Patent is hereby corrected as shown below:

In column 4, lines 66-68 (in EXAMPLE 8) (and continued in column 5, line 4), please indent the ingredients for Grain mix as follows:

Grain mix
        whole ground oats 10%
        whole ground soybeans 10%
        whole ground corn 70%
        whole ground wheat 10%

Signed and Sealed this

Fourteenth Day of June, 1988

Attest:

DONALD J. QUIGG

Attesting Officer

Commissioner of Patents and Trademarks